United States Patent [19]

Pouletty et al.

[11] Patent Number: 5,843,440
[45] Date of Patent: Dec. 1, 1998

[54] CELLULAR AND SERUM PROTEIN ANCHORS FOR MODULATING PHARMACOKINETICS

[75] Inventors: Philippe Pouletty; Christine Pouletty, both of Atherton, Calif.

[73] Assignee: RedCell Canada, Inc., Montreal, Canada

[21] Appl. No.: 702,127

[22] Filed: Aug. 14, 1996

Related U.S. Application Data

[63] Continuation of Ser. No. 137,821, Oct. 15, 1993, abandoned, which is a continuation-in-part of Ser. No. 70,092, May 27, 1993, abandoned, which is a continuation-in-part of Ser. No. 592,214, Oct. 3, 1990, abandoned.

[51] Int. Cl.⁶ .................. A61K 39/395; C07K 16/18; C07K 16/28; C07K 16/44

[52] U.S. Cl. .................. 424/133.1; 424/136.1; 424/153.1; 424/173.1; 424/175.1; 530/387.3; 530/388.7; 530/388.85; 530/388.9; 530/389.6; 530/389.1; 530/389.8

[58] Field of Search ............... 424/132.1, 133.1, 424/136.1, 153.1, 173.1, 175.1; 530/387.3, 388.7, 388.9, 388.85, 389.6, 389.1, 389.8

[56] References Cited

PUBLICATIONS

Koolwijk et al. Molecular Immunology vol. 28 No. 6 pp. 567–576 1991.
Titus et al. Journal of Immunology 139:9–3153–3158 1987.
Taylor et al. PNAS 88 pp. 3305–3309 1991.
Taylor et al. Journal of Immunology 148:8 pp. 2462–2468 1992 (Apr. 15).
Harris et al. TibTech 1993 (vol. 11) p. 42.
Hjrd et al. Genes and Cancer Ed. Carney & Sikora et al. 1990 p. 183.
Waldmann Science vol. 252 p. 1657, 1991.

*Primary Examiner*—Toni R. Scheiner
*Assistant Examiner*—Nancy A. Johnson
*Attorney, Agent, or Firm*—Limbach & Limbach L.L.P.

[57] ABSTRACT

Novel bifunctional reagents useful in reducing the biological effect of an undesirable blood-borne agent are provided. The reagents comprise conjugates of a first binding member specific for a blood-borne agent having a detrimental biological activity in a mammalina host, such as a growth factor, coagulation factor, enzyme, toxin, drug of abuse, microbe, autoreactive immune cell, infected or tumorous cell, joined to an second binding member specific for an anchor, where the anchor is a long-lived blood component, including cells, such as a erythrocyte, platelet or endothelial cell and serum proteins, such as albumin, ferritin, or steroid binding proteins. These conjugates find therapeutic use by coupling the agent and the blood component and thereby reducing the biological activity or effective concentration of free agent, modulating the volume of distribution of the agent, targeting the agent to sites of enhanced immune response, or facilitating agent clearance from the bloodstream.

8 Claims, No Drawings

CELLULAR AND SERUM PROTEIN ANCHORS FOR MODULATING PHARMACOKINETICS

CROSS REFERENCE TO RELATED APPLICATION

This application is a continuation of application Ser. No. 08/137,821, filed Oct. 15, 1993, now abandoned, which is a continuation-in-part of application Ser. No. 08/070,092 filed May 27, 1993, now abandoned, which is a continuation-in-part of application Ser. No. 07/592,214 filed Oct. 3, 1990, now abandoned, the entire disclosures of which is incorporated herein by reference.

TECHNICAL FIELD

The field of this invention is the diminution of the pathological or pathological activity of entities which may be found in blood.

BACKGROUND

It is frequently desirable to limit the biologic effects of agents present in the mammalian blood stream. For example in the case of exposure to a toxin/poison, acute mitigation of the effects of the toxin/poison may be indicated. Alternatively, the agent may be cellular as an infected, autoreactive or tumorous host cell or an infectious organism.

Present blood therapies involve removing the agent from the blood by for example, plasmapheresis or adsorption with activated charcoal, disruption of the agent with for instance, antibiotics or enzymes, or the selective binding of the target, for example with antibodies. These therapies are normally employed after the patient has been exposed to the deleterious effects of the toxin/poison or the cells, so that substantial damage to the host has already occurred.

There is, therefore, substantial interest in being able to provide for improved methods of limiting the toxicity or pathogenicity of blood-borne agents.

SUMMARY OF THE INVENTION

Bifunctional reagents useful in reducing the biologically effective concentration of an undesirable blood-borne target agent are provided. The reagents comprise a conjugate of first and second binding members: a first binding member binding specifically to the blood-borne agent; and a second binding member or anchor, which specifically binds to a long-lived blood associated entity. These conjugates find broad therapeutic applications where it is desirable to reduce the biologically effective concentration of an agent in blood.

Target agents may be host derived or foreign. Target host agents include cells and blood compounds present in undesirable concentrations such as autoreactive white cells, infected cells, tumorous cells, and overexpressed cytokines and hormones. Target foreign agents include toxins, poisons, drugs of abuse, pathogenic infectious microbes, or the like.

The long-lived blood associated entities include long-lived serum proteins, erythrocytes, platelets or endothelial cells, where the anchor binding member binds to one or more surface membrane proteins predominantly associated with the particular cell. In the case of erythrocytes and platelets, the conjugate may be administered pre-bound to the cells.

DESCRIPTION OF THE SPECIFIC EMBODIMENTS

Methods and compositions are provided for treating a mammalian host to diminish the detrimental biological effects of a deleterious blood-borne target agent present in the host's blood by administering in vivo a conjugate comprising a conjugate of first and second binding members: a first binding member binding specifically to the blood-borne target agent; and a second binding member, which specifically binds to a long-lived blood associated entity, the "anchor," whereby a reduction in the biologically effective concentration or physiological activity of the target agent is achieved. Effective concentration means the agent concentration that is immediately bioavailable to the target's in vivo site of action. Thus, the effective concentration of a toxin or poison, for instance, is the bioavailability to the cellular system responsive to such toxin or poison. Of course, with many agents, the site of action will vary with the physiological condition of the host, the concentration of the agent, etc. Generally, the target agents will be at least partially dispersed in the blood stream, may be in solution or associated with components of the blood stream. Thus the effective concentration may be reduced by limiting the volume of distribution of the target agent as to sites at which the target agent is segregated, by limiting diffusion, mobility, or migration of the agent, etc.

The disclosed therapeutic methods are applicable to a broad range of target agents, both host derived and foreign (meaning exogenous or non-host), which may be present in the blood and have a deleterious physiological effect, due to an undesirably high effective concentration, or as in the case of neoplastic cells, being present in any amount. Host derived cellular target agents include, (with parenthetical clinical indication): T cell or subsets such as CD4+, 8+ or LFA1+ cells (autoimmune disease, alloreactivity and inflammation), B cells or subsets such as pre-B cells, IgE+, IgM+ etc. (B cell lymphoma, xenograft, autoimmunity, anaphylaxy), leukocytes, such as macrophages and monocytes (inflammation, myelomonocytic leukemia), other leukocytes such as neutrophils, basophils, NK cells eosinophils, or allo- or xeno-reactive leukocytes, etc. (inflammation, anaphylaxis), stem cells such as CD34+ cells (polycythemia), malignant cells (malignancies; CALLA) or infected cells, particulaly HIV infected host cells, or the like.

Host derived non-cellular target agents include soluble HLA, class I and class II, and non-classical class I HLA (E, F and G) for modulating immunoregulation, soluble T or B cell surface proteins, cytokines, interleukins and growth factors such as IL 1, 2, 3, 4, 6, 10, soluble IL2 receptor, M-CSF, G-CSF, GM-CSF, platelet growth factos, alpha, beta, and gamma interferons, TNF, NGFs, arachadonic acid metabolites such as prostaglandins, leukotrienes, thromboxane and prostacyclin for cardiovascular diseases, immunoglobulins such as total IgE for anaphylaxy, specific anti-allergen IgE, auto or allo-antibodies for autoimmunity or allo- or xenoimmunity, Ig Fc receptors or Fc receptor binding factors, erythropoietin, angiogenesis factors, adhesion molecules, MIF, MAF, complement factors, PAF aceter, ions such as calcium, potassium, magnesium, aluminum, iron, etc, enzymes such as proteases, kinases, phosphatases, DNAses, RNAses, lipases and other enzymes affecting cholesterol and other lipid metabolism, esterases, dehydrogenases, oxidases, hydrolases, sulphatases, cyclases, transferases, transaminases, atriopeptidases, carboxylases and decarboxylases and their natural substrates or analogs, superoxide dismutase, hormones such as TSH, FSH, LH, Thyroxine (T4 and T3), renin, insulin, apolipoproteins, LDL, VLDL, dehydroepiandrosterone, cortisol, aldosterone, estriol, estradiol, progesterone, testosterone, dehydroepiandrosterone (DHEA) and its sulfate (DHEA-S), calcitonin, parathyroid hormone (PTH), human growth hormone (hGH), vasopressin and antidiuretic hormone (ADH), prolactin, ACTH, LHRH, THRH, VIP, cathecolamines (adrenaline, vanillylmandelic acid, etc.), bradykinins and corresponding prohormones, metabolites, ligands or natural cell or soluble receptors thereof, cofactors including atrionatriuretic factor (ANF), vitamins A, B, C, D, E and K serotonin, coagulation factors, e.g. thrombin, fibrin, fibrinogen, Factor VIII, Factor XI, von Willebrand factor, tissue plasminogen activator, or other factors, complement activation factors, LDL and ligands thereof, uric acid, etc.

Foreign target agents include drugs, especially drugs subject to abuse such as heroin and other opiates, PCP, barbiturates, cocaine and derivatives thereof, benzodiazepins, etc., poisons, toxins such as heavy metals like mercury and lead, chemotherapeutic agents, paracetamol, digoxin, free radicals, arsenic, bacterial toxins such as LPS and other gram negative toxins, Staphylococcus Toxins, Toxin A, Tetanus toxins, Diphtheria toxin and Pertussis toxins, plant and marine toxins, virulence factors, such as aerobactins, radioactive compounds or pathogenic microbes or fragments thereof, including infectious viruses, such as hepatitis B, A, C, E and delta, CMV, HSV (type 1, 2 & 6), EBV, varicella zoster virus (VZV), HIV-1, -2 and other retroviruses, adenovirus, rotavirus, influenzae, rhinovirus, parvovirus, rubella, measles, polio, reovirus, orthomixovirus, paramyxovirus, papovavirus, poxvirus and picornavirus, prions, protists such as plasmodia tissue factor, toxoplasma, filaria, kala-azar, bilharziose, entamoeba histolitica and giardia, and bacteria, particularly gram-negative bacteria responsible for sepsis and nosocomial infections such as *E. coli*, Acynetobacter, Pseudomonas, Proteus and Klebsiella, but also gram positive bacteria such as staphylococcus, streptococcus, etc. Meningococcus and Mycobacteria, Chlamydiae, Legionnella and Anaerobes, fungi such as Candida, *Pneumocystis carini,* and Aspergillus, and Mycoplasma such as Hominis and *Ureaplasma urealyticum.*

Coupled to the target agent-specific binding member is a high affinity binding member for a long-lived blood associated component; particularly for a long-lived serum protein or a binding site substantially specific to red blood cells, platelets or endothelial cells, preferably erythrocytes or platelets, more preferably erythrocytes.

The choice of the blood associated component serving as the anchor entity will be affected by the manner in which the effect of the target agent is to be diminished. Thus depending on the choice of the anchor entity, the target agent may be rapidly segregated and excreted from the body, segregated in a biologically inactive form to be slowly eliminated, or degraded over time. The anchor may be fixed or mobile, that is, substantially fixed in position, as in the case of the endothelial cells, or mobile in the vascular system, having a substantially uniform or variant distribution in the vascular system, where the anchor may be preferentially present in particular compartments, including solid tissue. The choice of long-lived blood component will also depend in part on the nature of the pathogenic agent. For instance, red blood cells are preferred for cellular pathogenic agents for efficient clearance, while serum protein components, such as albumin, are particularly useful for segregating soluble toxins.

A long-lived blood component has a half-life of at least about 12 hrs, preferably at least about 48 hrs, more preferably at least about 5 days. Generally, half-lives are determined by serial measurements of whole blood, plasma or serum levels of the compound following labelling of the compound with an isotope (e.g. $^{131}I$, $^{125}I$, Tc, $^{51}Cr$ $^{3}H$ etc) or fluorochrome and injection of a known quantity of labelled compound I.V. Included are red blood cells (half life ca. 60 days), platelets (half life ca. 4–7 days), endothelial cells lining the blood vasculature, and long lived blood serum proteins, such as albumin, steroid binding proteins, ferritin, α-2-macroglobulin, transferrin, thyroxin binding protein, immunoglobulins, especially IgG, or only the Fc portion, etc. In addition to preferred half-lives, the subject components are preferably in cell count or concentration sufficient to allow binding of therapeutically useful amounts of the conjugate. For cellular long lived blood components, cell counts of at least 2,000/$\mu$l and serum protein concentrations of at least 1 $\mu$g/ml are preferred.

The selected cellular long-lived blood components are present in high number in the vascular system. Platelets are present in from about 1–4×$10^5$/$\mu$l, while red blood cells are present in about 4–6×$10^6$/$\mu$l. The cells have a long half-life and by appropriate choice of binding site of a surface membrane protein, e.g. epitope for binding to antibodies, endocytosis is avoided. The erythrocyte and platelets lack a nucleus and cell division capability. Preferred cells have a wide distribution in capillaries and tissue and express specific binding sites on the cell surface associated with their specific differentiation. In addition to in vivo administration of the subject conjugate, in the case of red blood cells and platelets, these cells may be readily collected, combined with the conjugate, and then administered to the host. The cells may be autologous or allogenic.

The choice of the long-lived blood component anchor also depends on the desired route of limiting the agent's toxicity/pathogenicity. For instance, it is often desirable to modulate an agent's access to the central nervous system, interstitial spaces, etc. to limit toxicity, infection, etc. By selecting the anchor based on location, distribution, specific surface markers, or other differentiating characterisitc associated with the anchor, one can modulate the ultimate sites and volume of distribution of the agents. For example, in some situations cellular activation results in up-regulation of a surface membrane protein. For endothelial cells, addressing, e.g. ELAM-1, or integrins, e.g. VLA-4, may be up-regulated in the case of inflammation. In this way, the agent may be segregated to a site of inflammation or lymphoid organ such as the spleen to enhance the agents exposure to a concentrated immune response including phagocytic white cells. In another example, the immune complexes of a complement binding antibody can provide for complement mediated lysis of cells or microorganisms.

In referring to a specific binding site is intended a particular spatial conformation and charge distribution which has a high affinity to a complementary molecule, which has the reciprocal conformation and charge distribution. Thus in the case of the anchor and conjugate anchor specific binding member or the target agent and the conjugate target agent specific binding member, the conjugate will be selected to preferentially bind to its complementary binding member, as compared to the numerous other molecules which may be encountered associated with the vascular system. Examples of binding sites include immunological epitopes (an epitope to which an antibody or TCR binds), sugar moieties (binding sites to which a lectin binds), peptide-specific binding sites (binding sites to which peptides bind, as in ligand and cell surface membrane receptor), nucleic acid specific binding sites (sequences to which single stranded nucleic acid sequences hybridize), synthetic or naturally occurring organic compound specific binding sites (haptens binding to antibodies or organic agonists or antagonists to naturally occurring ligands), etc. Suitable erythrocyte binding site containing molecules include glycophorin A, B and C, Band 3 and Rhesus blood group antigens. Preferred erythrocyte binding sites are abundantly expressed on the erythrocyte with copy numbers of at least 1,000, preferably at least 10,000, more preferably at least 100,000 per cell, desirably are tethered at least about 0.5, preferably at least about 1 nm, above the bilayer surface and do not facilitate cell deformation when the conjugate is bound to the anchor (e.g. the binding will be selected so as not to be a component of the cytoskeleton). Binding sites of the erythrocyte surface glycoprotein glycophorin A and erythrocyte binding sites comprising sialic acid are examples of preferred binding sites. Preferred platelet binding sites include GPIIa, GPIIb, GPIIIa and GPIV. Desirably, upon binding to the the target agent, deformation of the cellular anchor, e.g. erythrocyte or platelet, occurs.

By "specific to" is meant that the binding site is present on a given target agent or anchor and substantially absent from blood associated components present during the presence of the conjugate. The presence of a given binding site is generally determined by the binding of a binding site specific reciprocal binding member. Anchor-specific binding sites or target agent specific binding sites are readily identified empirically by exploiting the ability of a binding site specific reciprocal binding member to distinguish blood associated components or target agents containing the anchor specific binding site or target agent specific binding site from blood associated components present in the host at the time of treatment. For example immunofluorescent microscopy, flow cytometry, cell panning, enzyme immunoassay (EIA), affinity chromatography, bead separation etc. may be used to assay binding site specificity for cellular targets and for molecular (proteins, glycoproteins, carbohydrates, lipids, organics, molecular toxins, etc) targets, respectively. By employing blood free of the anchor or target agent in a competitive assay with labeled anchor or target agent, a reduction in the level of binding of the anchor or target agent in the presence of blood as compared to the level of binding in the absence of blood would indicate cross-reactivity of a blood component with the anchor or target agent, respectively. Where a reciprocal specific binding member (reciprocal to the anchor or target agent) is introduced into the host, generally, more than about fifty percent (50%), preferably more than about seventy-five percent (75%) of the reciprocal binding member, which are bound to the binding site of the anchor or target agent after administration, will be bound to the anchor or target agent. Where binding assays are optimized, specific receptor-epitope binding will have a binding affinity of at least about $10^{-6}$M, preferably at least about $10^{-7}$M, more preferably in the range of about $10^{-8}$M to $10^{-11}$M, under physiological conditions.

The reciprocal binding site members of the conjugate may be derived from any molecule capable of providing the requisite anchor or target agent binding specificity that is compatible with in vivo use. The two binding sites of the conjugate will be directed to different complementary binding members, normally on different target agents. The conjugate binding members may be derived from a natural receptor or ligand of the anchor or target agent: Examples include enzymes and substrates or cofactors, lectins and sugars, antibodies or T-cell antigen receptors and immunological epitopes, cytokines (e.g interleukins) or hormones (e.g. LH) or drugs (e.g.opiates) or viruses (e.g. HIV) or immunoglobulin (e.g. IgE) and their respective receptors, (e.g CD4, Fc receptor, etc.) , etc., or truncated versions thereof or fragments of these molecules. For targeting some toxins such as heavy metals, chelators such as EDTA or EGTA, provide useful receptors. Alternatively, conjugate binding members may be specifically selected or synthesized to specifically bind the complementary binding member. For example, useful peptides, carbohydrates, nucleic acids, poly- and monoheterocyclic natural organics and synthetic molecules are isolated by screening natural or synthetic libraries for the requisite binding specificity. Typically, specific binding molecules are assayed by EIA, RIA, fluorescence, chemiluminescence, direct binding assays or competition assays by displacement of labelled agonist as described previously.

Conveniently, the conjugate binding members will include from one to two monoclonal antibodies or fragments thereof. The antibody or fragment thereof may be any one of the subtypes or isotypes, only being one that does not participate in complement effected lysis. Therefore, the whole antibody may be IgA, IgD, IgG1 or IgG4 or corresponding isotypes of other species, while fragments may be from any isotype. Normally, the antibody will be one which is allogenic, although xenogeneic antibodies may be employed, e.g. in those situations where the host is immunocompromised, or the antibody or fragment is non-antigenic, despite its being xenogeneic. To minimize the immune response while maintaining the convenience of using non-human antibodies, it is often desirable to generate chimeric antibodies. The whole antibody need not be used, fragments being frequently useful, such as Fv, Fab, F(ab')2, the heavy chain, a single-chain antigen binding protein, a peptide conformer mimicking an antibody binding site, or the like. Thus, only the binding site of the antibody may be used, which will usually comprise the variable regions of the heavy and light chains, although in some instances, only the heavy or light subunit variable region may suffice. The fragment which is used, should retain at least a substantial portion, preferably at least about ten percent of the original affinity of the antibody; or following selected mutations, may exhibit a higher affinity.

Monoclonal antibodies may be obtained in accordance with conventional ways. For monoclonal antibodies specific for red blood cells, lymphocytes may be collected from an individual with a positive direct Coombs test, particularly of the IgG type, (without complement) without a showing of hemolysis. The lymphocytes may be immortalized by any convenient means, e.g. Epstein-Barr virus transformation, cell fusion, cell transfection, or the like, followed by screening for antibodies having the desired specificity and affinity, as well as the desired isotype. The antibodies may then be modified in a variety of ways, by enzymatic cleavage to provide for fragments, using papain, chymotrypsin, pepsin, trypsin, reduction with cleavage of intramolecular disulfide linkages or the like. The antibodies may be from any source, such as primate, particularly human, murine, lagomorpha, canine, ovine, porcine, equine, or the like or genes coding for at least one region of the antibody may be cloned and expressed in procaryotic or eukaryotic expression systems.

Conjugate binding members which bind to red blood cell anchors may be further characterized by binding to ORh negative erythrocytes or to panels of erythrocytes of known phenotypes. Those conjugate binding members which react with substantially all the cells (at least 80%) of the panel and, furthermore, show negative results with the direct Coombs test using anti-complement globulin are selected. Ref: Stratton, F.; Rawlinson, Vi; Merry, A. H.; Thomson, E. E.; *Clin. Lab. Haematol.* 1983, 5:17–21. In addition, the antibodies are screened as to cross-reactivity with blood associated components, particularly cells, such a lymphocytes, myelomonocytes, platelets, and the like, and serum proteins. Similarly, for antibodies specific for the anchors comprising long-lived serum proteins, platelets or endothelial cells, the antibodies are selected to be specific for such proteins/cells and not for other proteins/cells which may be encountered in the host. For the most part, with red blood cells the number of conjugates bound per cell (when not bound to the blood borne target) will be below the level that causes hemolysis.

If desired, the antibodies can be prepared or modified in a variety of ways. Chimeric antibodies may be prepared, where the constant region may be modified as to isotype or species. For example, murine monoclonal antibodies may be prepared, the genes encoding the heavy and light chains isolated, and the constant regions of the heavy and light chains substituted with the appropriate constant regions of human constant regions to provide for a chimeric antibody which lacks the antigenicity of the murine constant region. Alternatively, variable regions obtained from a host may be cloned and mutated and then screened to identify specific binding affinities. A further alternative is to exchange not only the constant region of the heavy and light chain, but also exchange the framework regions of the variable domains, so as to further reduce the antigenicity of the antibody. Numerous techniques are described in the literature, for example, "The synthesis and in vivo assembly of functional antibodies in yeast," Wood, C. R., Boss, M. A., Kenten, J. H., Calvert, J. E., Roberts, N. A., Emtage, J. S., Nature, Apr. 4–10, 1985, 314(6010):446–9; "Construction of chimaeric processed immunoglobulin genes containing mouse variable and human constant region sequences," Takeda, S., Naito, T., Hama, K., Noma, T., Honjo, T., Nature, Apr. 4–10, 1985, 314(6010):452–4; "A recombinant immunotoxin consisting of two antibody variable domains fused to Pseudomonas exotoxin," Chaudhary, V. K., Queen, C., Junghns, R. P., Waldmann, T. A., FitzGerald, D. J., Pastan, I, Laboratory of Molecular Biology, DCBD, National Cancer Institute, Bethesda, Md. 20892, Nature, Jun. 1, 1989, 339(6223):394–7; "Binding activities of a repertoire of single immunoglobulin variable domains secreted from Escherichia coli [see comments]," Ward, E. S., Gussow, D., Griffiths, A. D., Jones, P. T., Winter, G., MRC Laboratory of Molecular Biology, Cambridge, UK, Nature (ENGLAND), Oct. 12, 1989, 341(6242):544–6, ISSN 0028–0836, Comment in Nature, 1989, Oct. 12, 341(6242):484–5.

Instead of antibodies, other binding molecules may be employed which are specific for the anchor. The anchor binding member may be a naturally occurring or synthetic molecule or modified, e.g. truncated or mutated, derivative thereof. Compounds, such as drugs, e.g. penicillin, $T_3$, $T_4$, cortisol, cholesterol, etc., hormones, glycoproteins from microorganisms, e.g. viruses, such as reovirus, rubella virus, influenzae virus, HIV, CMV, etc., have binding sites which are specific for such anchors as red cells, serum albumin, thyroxine binding protein, steroid binding protein, etc. For Ig Fc, one use protein A, protein G, or other specific binding protein for the Fc, or desirably fragments thereof which substantially retain the binding affinity of the entire protein. In some instances, it will be desirable to modify the binding molecule to maintain its binding affinity, while diminishing other biological activity. This will be frequently achieved by the choice of site for linking the anchor binding member to the target agent binding member.

The conjugate may be prepared in any convenient way, depending on the nature of the binding member components of the conjugate, the need to maintain the binding capability of the binding members and such other considerations as are relevant to the use of the conjugate in vivo. Depending on the nature of the conjugate, the coupling ratio between the two binding members of the conjugate may vary from one to having a plurality of one or both of the binding members, there usually being on the average not more than 6, more usually not more than three of either of the binding members in the conjugate. Generally the anchor binding member will be one, but may be more than one where enhanced affinity for the anchor is desired.

The nature of the linkage between the binding members of the conjugate will vary widely depending upon the chemical composition of the binding members. Generally, stable linkages are preferred and covalent linkages are especially preferred. By "stable" is intended that the linkage will not be preferentially cleaved as compared to other bonds in the molecule; "unstable" intends preferential cleavage. However, occasionally one may wish to permit limited time-course degradation of the linkage. For example, in some cases one may wish to have controlled release of the complex of the conjugate and the target agent, where the affinities of the binding members of the conjugate are very high. By providing for cleavage or degradation of the conjugate the target agent will be released in accordance with the rate of cleavage or degradation of the conjugate, rather than the off rate of the target agent from the complex. A wide variety of linkages will be unstable under physiological conditions, where the instability may be as a result of enzymatic or non-enzymatic reactions. For example, ester linkages can be provided which are relatively labile and will be cleaved over time in the blood stream. By providing for varying degrees of steric hindrance, different degrees of lability can be achieved. Alternatively, sequences can be provided, which are recognized by a wide variety of enzymes such as proteases. For example, a series of arginine-lysine dimeric units will be sensitive to trypsin. Other protease labile linkages may be employed, where the protease may be found in the bloodstream. Alternatively, one may employ disulfide linkages, which will be subject to reductive cleavage. Other functionalities which may find use include oligosaccharides, thiol esters, nucleic acids, or the like. Alternatively, one may rely upon the nature of one or both of binding members to provide for release of the target agent from the anchor, e.g. peptide nature of antibodies subject to proteases.

There are extensive reports in the literature of procedures for covalently joining a wide variety of compounds to prepare conjugates with different functional groups. Various synthetic schemes may be envisioned, again depending upon the nature of the conjugate binding members. Thus, where sulfhydryl groups are present, these may be readily activated to provide for linkage to a sulfhydryl group to provide a disulfide or with a maleimide group, where a thiol may bind to the maleimide to provide for a thioether. Carboxyl groups may be readily activated with a wide variety of hydroxyl compounds or carbodiimide, where the ester or anhydride is allowed to react with hydroxyl or amino groups to provide esters or amides. Analogously, saccharide moites can be activated with periodate. Other linkages may also find application, such as imines, hydrazines, etc. Alternatively, non-covalent linkages may be used, such as biotin-avidin linkages, double antibody linkages, lectin-saccharide linkages, and the like. Where the conjugate binding members are both proteins, such as antibodies or fragments, the conjugate may be genetically engineered as a single construct, cloned and expressed using a variety of vectors and host cells. Alternatively, the two conjugate binding members can be recombinantly or chemically synthesized and subsequently coupled, particularly by affording unique functionalities available for coupling. Chemical synthesis may employ commercially available synthesizers using liquid or solid phase synthesis, where the synthesis may be all or a part of the conjugate.

The subject compositions may be used for the treatment, prophylactic or therapeutic, of a wide variety of cellular diseases, toxicities and environmental exposures and may be administered in a wide variety of ways, depending on the indication. If desired, the conjugate may be first bound to the long-lived blood component in appropriate proportion followed by administration. Alternatively, the conjugate may be administered to the host for binding to the anchor cells or proteins. The amount of the conjugate which is administered will vary widely, depending upon the nature of the conjugate, the purpose for the conjugate, the therapeutic dosage, the physiological activity of the compound when present as a conjugate, and when bound to a cell, and the like. Therefore, the amount of conjugate administered to a host may vary from 1 $\mu$g to 50 mg/kg of host.

The subject compositions will, for the most part, be administered parenterally, such as intravascularly (IV), intraarterially, intramuscularly (IM), subcutaneously (SC), or the like. Administration wil normally be by transfusion if the conjugate is bound to cells. If the conjugate is unbound, administration will normally be IV, IM or SC. Where the compositions are of low molecular weight (less than about 10 kD) or resistant to digestive enzymes, conjugate administration may be oral, nasal, rectal, transdermal or aerosol, where the nature of the conjugate allows for transfer to the vascular system. Physiologically acceptable carriers will usually be employed, such as water, saline, phosphate buffered saline, aqueous ethanol, plasma, proteinaceous solutions, glucose or mannitol solutions, or the like. The concentration of the conjugate will vary widely, generally ranging from about 1 pg/ml to 50 mg/ml. Other additives which may be included include buffers, where the media are generally buffered at a pH in the range of about 5 to 10, where the buffer will generally range in concentration from about 50 to 250 mM, salt, where the concentration of salt will generally range from about 5 to 500 mM, physiologically acceptable stabilizers, and the like. The compositions may be lyophilized for convenient storage and transport.

The choice of the anchor will affect the manner in which the biological activity of the target agent is modified. Depending on the nature of the target agent different anchors will be employed. Where the target agent is a molecule, such as a small organic molecule or peptide, serum proteins will be satisfactory anchors, and elimination of the target agent will accompany elimination of the serum protein. The target agent must be substantially inactivated while bound to the conjugate, particularly where the target agent has cytotoxic effects. Where the target agent is a virus particle or cell, usually the anchor will be a cell, the choice of cell depending upon whether one wishes to have the target cell rapidly eliminated or maintained in the host segregated to particular cellular compartments. For example, if one wishes to eliminate virus infected cells or neoplastic cells, the anchor would be erythrocytes or platelets, so that the target cell would become bound to the erythrocytes or platelets to prevent the target cell to enter small vessels and the complex recognized by the spleen for elimination. With erythrocytes, the deformation of the erythrocytes on binding to the target cell aids in the recognition of the complex for elimination. A similar mechanism is operative for platelets.

The subject invention may be used in chronic or acute situations, either prophylactic or therapeutic. For acute situations, the conjugate will normally be administered in anticipation of the acute situation. For example with drug addicts, one may wish to prevent the use of a particular drug of abuse, particularly where the patient is on a methadone program. By administering the subject conjugate, where the conjugate may exert an effective binding capability of weeks or months, taking of the drug of abuse would result in its inactivation, inhibiting the euphoric effect. Similarly, where one is concerned about nosocomial infection, one would administer the conjugate in anticipation of the infection, so that upon infection, the toxin or tumor necrosis factor would become bound to diminish its effective concentration below a pathological level.

The subject conjugates can be presented as one or a few molecules bound to the cellular blood associated entity or there may be a large number of conjugates, e.g. 10 to $10^6$, bound to the blood associated entity. The higher levels of binding may be achieved by combining the conjugate with the blood associated entity in vitro. In this way, depending on the target agent, the multivalent activity can provide for much greater effectiveness or biological activity of the conjugate, particularly as to the inactivation and/or elimination of target cells.

For therapeutic use, one could administer the conjugate to a cancer patient, so that the blood would be monitored for metastatic cells or growth factor excess. In this case, one would use an anchor which provides for rapid elimination, such as erythrocytes. Where cells are not normally found in the vascular system, sush as mammary cells, the conjugate would have as the target protein, a mammary cell surface protein, so that any mammary cells in the vascular system could be detected and eliminated. In the case of T cells involved with autoimmune disease, where such cells have a common epitope, the conjugate would surveil the blood for such cells and be able to bind to such cells and eliminate the cells by the mechanisms indicated above.

The subject invention can be used in anticipation of one or more events which may have deleterious physiological effects, e.g. drug ingestion or adverse physiological response of a host to trauma or surgery, or for a chronic situation where the continued production of toxins, virus particles or the like, as a result of an intractable infection, is continuously monitored by the conjugate bound to a long lived anchor. The subject invention provides a long-lived source of binding capability, where upon binding of a target agent, the deleterious biological effects of the target agent are rapidly diminished and the target agent may be slowly or rapdily eliminated for the host by a variety of natural mechanisms associated with degradation, chemical modification, elimination of modified or defective erythrocytes and platelets.

The following examples are offered by way of illustration and the way of implementation.

EXPERIMENTAL

Example 1

Modification of Cocaine Volume of Distribution

A monoclonal antibody raised against a cocaine-BSA conjugate (molar ratio, 10:1) using BALB/c mice and SP20 myeloma is screened by solid phase microtiter plate ELISA against Cocaine-BSA and irrelevant peptide-BSA as control antigen. Selected antibodies specificity is verified by competition assay against cocaine-BSA in which binding of antibodies is inhibited in a dose dependent manner by free cocaine. Selected antibody is IgG1, with a supernatant titer by ELISA of 1:64. Mab is produced in ascites fluid and purified by protein A affinity chromatography.

Anti-RBC Mab is an IgG1 Mab specific for human glycophorin A and reacting with blood group antigen M (obtained from Hospital Saint-Louis, Paris). The Mab cross-reacts with chimpanzee and *Macaccus muliata* erythrocytes.

Fab fragments (produced by papain digestion monitored by SDS-PAGE) from both anti-RBC and anti-cocaine Mabs are conjugated using the Nakane method, in which the first member of the conjugate is activated by sodium periodate, before addition of the second member of the conjugate, resulting in a carbohydrate-NH2 residue covalent coupling. pH is monitored during coupling reaction and ratios of both members are optimized to provide a mean molar ratio close to 1:1. Conjugate is purified by gel filtration. The pics corresponding to molecular weight between 80 KD and 120 KD (determined by SDS PAGE) are selected. Reactivity of conjugate with cocaine is verified by ELISA as above, using an anti-mouse kappa chain specific peroxidase conjugate, and as control an anti-mouse Fc specific peroxidase conjugate (which does not react with cocaine bound Fab). Reactivity of conjugate with human RBC is tested by flow cytometry using anti-mouse Fab FITC conjugate and as control an anti-mouse Fc specific FITC conjugate (which does not react with cocaine bound Fab). The conjugate is shown not to agglutinate RBCs and not to induce hemolysis (between 100 ng/mL and 10 $\mu$g/mL) when incubated in human and monkey plasma with addition of fresh rabbit complement.

The biodistribution of $^{125}$I labelled cocaine is evaluated with and without pretreatment of animals with anti-RBC, cocaine specific conjugate. Animals (n=3) receive IV by slow injection (5 minutes) 50 $\mu$g/Kg of conjugate diluted in glucose 5% with 1% of human serum albumin. Five days after the injection, animals receive 10 $\mu$curie of $^{125}$I-labelled cocaine IV (100 $\mu$g per animal). 1 hour after the cocaine injection, animals are sacrificed, and various blood and tissue specimens are collected, including brain specimens (frontal and occipital cortex).

Control animals (n=3) receive only $^{125}$I labelled cocaine and no conjugate. Specific radioactivity is measured using a gamma counter, and expressed in cpm per ml of blood or cpm per gram of tissue. Animals which receive the conjugate pre-treatment have an average brain $^{125}$I specific activity of 2.2% (+/−0.7%) the average brain $^{125}$I specific activity of control animals, and a mean whole blood specific activity of 25 times (+/−4) that of control animals (with a ratio of erythrocyte to plasma $^{125}$I specific activity of 20:1 in the conjugate treated group, and 0.2 in the control group).

The results demonstrate that pre-treatment with a erythrocyte-anchor specific for cocaine modifies the cocaine volume of distribution, decreases diffusion of cocaine into the central nervous system, and decreases the ratio of plasma to erythrocyte cocaine concentration (with a net increase in whole blood concentration).

Example 2

Anti-T cell Subset Conjugate

A rat anti-mouse RBC specific Fab fragment is conjugated to purified recombinant HIV1 gp120 (Molar ratio 1:2). Following IV administration to SCID Hu mice (10 $\mu$ per mouse) of the RBC/gp 120 anchor, whole blood specimens are collected serially in the following 48 hours, and analyzed by fluorescent microscopy and flow cytometry. In the first 6 hours, rosettes of erythrocytes and CD3+, CD4+, CD8− T cells are observed in the animals pretreated with the Anchor, and are absent in control animals.

Example 3

Anti-Viral Protein Anchor

A rat anti-mouse RBC specific Fab fragment is conjugated to purified recombinant CD4 (Molar ratio 1:3). 48 hours following IV administration to BALB/c mice (10 $\mu$g per mouse) of the RBC/CD4 conjugate, $^{125}$I labelled recombinant HIV1 gp120 is injected IV to conjugate pretreated or control animals. Half-life (whole blood, erythrocyte and plasma) concentration of gp120 is measured in the following 24 hours and 8 days. The plasma half-life of gp120 is dramatically decreased in treated animals, whereas the erythrocyte and whole blood half lifes are increased.

The disclosed invention provides an improved method for limiting the pathogenic or toxic effects of agents present in the mammalian blood stream. The method finds application where surveillance is desired for the presence of physiologically detrimental agents in the blood stream. By providing for a conjugate which binds specifically to such agents and is bound to a long-lived blood associated component which enhances the life of the conjugate in the blood, the conjugate can act to bind and inactivate the agent, and by appropriate choice of the long-lived blood associated component, the agent can be slowly or rapidly eliminated from the host, using the normal physiological mechanisms for such elimination.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for extending the lifetime of a conjugate in the blood stream of a host, wherein said conjugate is capable of binding to a physiologically active target agent, said method comprising;

administering a conjugate to the blood stream of said host, said conjugate characterized by having one first and one second binding member, wherein said first binding member comprises an antibody or binding fragment thereof that binds specifically to erythrocytes, without lysis of said erythrocytes, and said second binding member comprises an antibody or binding fragment thereof that binds to said target agent;

whereby said conjugate binds to said erythrocytes and any target agent present in said blood stream of said host for an extended period of time.

2. A method according to claim 1, wherein said second binding member binds to a drug.

3. A method according to claim 1, wherein said first and second binding members are Fab fragments.

4. A method for extending the lifetime of a conjugate in the blood stream of a host, wherein said conjugate is capable of binding to a drug, said method comprising administering a conjugate to the blood stream of said host, said conjugate characterized by having one first and one second Fab fragment binding member, said first binding member binding specifically to erythrocytes, without lysis of said erythrocytes and said second binding member binding to said drug;

whereby said conjugate binds to said erythrocytes and any drug present in said blood stream of said host for an extended period of time.

5. A method according to claim 4, wherein said drug is a drug of abuse.

6. A method according to claim 5 wherein said drug of abuse is cocaine.

7. A method for extending the lifetime of a conjugate in the blood stream of a host, wherein said conjugate is capable of binding to cocaine, said method comprising;

administering a conjugate to the blood stream of said host, said conjugate characterized by having one first and one second binding member, wherein said first binding member comprises an antibody or binding fragment thereof that binds specifically to erythrocytes, without lysis of said erythrocytes, and said second binding member comprises an antibody or binding fragment thereof that binds to cocaine;

whereby said conjugate binds to said erythrocytes and any cocaine present in said blood stream of said host for an extended period of time.

8. A method according to claim 7 wherein said first and second binding members comprise Fab fragments.

* * * * *